(12) United States Patent
Niwa et al.

(10) Patent No.: US 10,069,250 B2
(45) Date of Patent: Sep. 4, 2018

(54) RECEPTACLE CONNECTOR

(71) Applicant: OLYMPUS CORPORATION, Tokyo (JP)

(72) Inventors: Hiroshi Niwa, Koganei (JP); Minoru Sato, Hino (JP); Koji Omori, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/678,224

(22) Filed: Aug. 16, 2017

(65) Prior Publication Data

US 2017/0340190 A1    Nov. 30, 2017

Related U.S. Application Data

(63) Continuation of application No. PCT/JP2016/061399, filed on Apr. 7, 2016.

(30) Foreign Application Priority Data

Jun. 15, 2015 (JP) ................................ 2015-120532

(51) Int. Cl.
*H01R 13/6591* (2011.01)
*A61B 1/00* (2006.01)
(Continued)

(52) U.S. Cl.
CPC ..... *H01R 13/6591* (2013.01); *A61B 1/00124* (2013.01); *H01R 13/652* (2013.01);
(Continued)

(58) Field of Classification Search
CPC ................................................ H01R 13/6591
See application file for complete search history.

(56) References Cited

U.S. PATENT DOCUMENTS 3,843,854 A * 10/1974 Mori ...................... H01H 13/18
200/51.09
5,772,466 A * 6/1998 Morin .................... H01R 24/62
439/489
(Continued)

FOREIGN PATENT DOCUMENTS

| JP | 61-248374 | 11/1986 |
| JP | 9-122082 | 5/1997 |
| WO | 2011/052408 A1 | 5/2011 |

OTHER PUBLICATIONS

International Search Report dated Jun. 21, 2016 received in International Application No. PCT/JP2016/061399.
(Continued)

*Primary Examiner* — James Harvey
(74) *Attorney, Agent, or Firm* — Scully, Scott, Murphy & Presser, P.C.

(57) ABSTRACT

The present invention provides a receptacle connector including: a grounding portion configured to ground a connection object; and a ground connection terminal that is configured to be switchably held in a first state in which the ground connection terminal is electrically separated from the grounding portion, or in a second state in which the ground connection terminal is electrically brought into conduction with the grounding portion. The ground connection terminal is switched between the first state and the second state in operative association with interlining of the plug connector and the fitting portion. In the first state, the grounding terminal and the grounding portion are electrically separated. In the second state, the grounding terminal and the grounding portion are electrically brought into conduction with each other through the ground connection terminal.

1 Claim, 5 Drawing Sheets

(51) Int. Cl.
　　　*H01R 13/652* 　　(2006.01)
　　　*H01R 13/707* 　　(2006.01)
　　　*H01R 13/703* 　　(2006.01)

(52) U.S. Cl.
　　　CPC ....... *H01R 13/707* (2013.01); *H01R 13/7036* (2013.01); *H01R 13/7039* (2013.01); *H01R 2201/12* (2013.01)

(56) References Cited

U.S. PATENT DOCUMENTS

| | | | | |
|---|---|---|---|---|
| 6,358,096 | B1* | 3/2002 | Beckman | H01R 13/7039 439/507 |
| 2011/0039444 | A1* | 2/2011 | Wu | H01R 13/641 439/490 |
| 2015/0374159 | A1* | 12/2015 | McRae | A47G 33/0872 439/108 |
| 2017/0223278 | A1* | 8/2017 | Ishizaki | H04N 5/23293 |
| 2017/0340190 | A1* | 11/2017 | Niwa | A61B 1/00124 |
| 2017/0347862 | A1* | 12/2017 | Yasunaga | A61B 1/00128 |

OTHER PUBLICATIONS

Japanese Notification of Reasons for Rejection dated Jan. 17, 2017 received in Japanese Patent Application No. 2016-564271, together with an English-language translation.

* cited by examiner

RECEPTACLE CONNECTOR

CROSS REFERENCE TO RELATED APPLICATION

This application is a continuation application of PCT/JP2016/061399 filed on Apr. 7, 2016 and claims benefit of Japanese Application No. 2015-120532 filed in Japan on Jun. 15, 2015, the entire contents of which are incorporated herein by this reference.

BACKGROUND OF THE INVENTION

1. Field of the Invention

This invention relates to a receptacle connector applicable to a medical device that is equipped with a plurality of receptacle connectors configured to enable the fitting and connection of a plug connector of an endoscope or the like.

2. Description of the Related Art

Endoscopes that are configured to have an insertion portion formed in an elongated shape are being widely utilized in, for example, a medical field and an industrial field. Among such endoscopes, medical endoscopes used in the medical field are configured so that an elongated insertion portion can be inserted into a body cavity of a subject to observe an organ inside the body cavity, or as necessary so that various kinds of treatment can be performed using a treatment instrument that is inserted into a treatment instrument insertion channel provided in the endoscope. Further, industrial endoscopes that are used in the industrial field are configured so that, by inserting an elongated insertion portion into an object, for example, into a jet engine or into piping in a plant, observation or inspection of the state inside the object, for example, observation or inspection of defects or corrosion, can be performed.

An endoscope of such kind is connected to, for example, an external apparatus (medical device) such as a video processor or a light source apparatus to construct an endoscope system by co-operation between the endoscope and the external apparatus. Therefore, in the endoscope system, the endoscope is configured to have a plug connector at an end part of a so-called "universal cable" in which various signal cables and light guide cables and the like that are extended from the endoscope are bundled. Further, in correspondence therewith, the aforementioned external apparatus is configured to have a receptacle connector that allows the plug connector on the endoscope side to be detachably attached to the receptacle connector, and that ensures an electrical connection between the endoscope and the external apparatus when the plug connector is fitted and connected. Note that a connector that is applied to a medical device such as an endoscope system is, in particular, referred to as a "connector for a medical device".

A connector for a medical device generally has a configuration such that, when a plug connector and a receptacle connector are fitted and connected together, a grounding terminal provided on the plug connector side and a ground connection terminal (finger terminal) provided on the receptacle connector side contact and are grounded by a grounding portion on the receptacle connector side, whereby an electromagnetic shield is formed that electromagnetically shields a connecting portion between contacts for communication, and by this means the emission of radiation noise and the like is restricted.

For example, a connector for a medical device disclosed in International Publication No. WO 2011/052408 is configured so that grounds of an endoscope and an external device are connected by fitting and connecting together a component made of metal provided on a plug connector side and a metal component provided on a receptacle connector side.

In this connection, in recent years, medical devices such as endoscope systems that have a configuration in which an internal ground circuit is made a common circuit while a plurality of receptacle connectors are provided on an external apparatus side (video processor or light source apparatus and the like) have come into practical use.

In a medical device of the above described form, in some cases the medical device is put into practical use in a state in which, for example, a plug connector is fitted into and connected to one receptacle connector among a plurality of receptacle connectors in an external apparatus, and a plug connector is not fitted into the other receptacle connectors, that is, the other receptacle connectors are in a vacant state.

In this case, because a fitting portion of a receptacle connector that is in a non-connected state with respect to a plug connector is open, there is a possibility that, for example, a finger of a person such as a user or conductive material of various kinds of instruments may be unintentionally inserted into the receptacle connector that is in the non-connected state. Accordingly, in a state in which a receptacle connector and a plug connector are not fitted together, it is desirable that an internal ground circuit and a ground connection terminal provided inside the fitting portion on the receptacle connector side be in an electrically isolated state.

SUMMARY OF THE INVENTION

A receptacle connector according to one aspect of the present invention includes a fitting portion into which a plug connector including a grounding terminal for forming an electromagnetic shield by being grounded can be fitted, the receptacle connector including: a grounding portion configured to ground a connection object by being electrically connected; and a ground connection terminal that is provided in the fitting portion and that is configured to be switchably held in a first state in which the ground connection terminal is electrically separated from the grounding portion when the fitting portion and the plug connector are not fitted together, or in a second state in which the ground connection terminal contacts and is electrically brought into conduction with the grounding portion when the fitting portion and the plug connector are fitted together; wherein: the ground connection terminal is switched between the first state and the second state in operative association with interfitting of the plug connector and the fitting portion; and the grounding terminal and the grounding portion are electrically separated at a time of the first state, and the grounding terminal and the grounding portion are electrically brought into conduction with each other through the ground connection terminal at a time of the second state.

DETAILED DESCRIPTION OF THE PREFERRED EMBODIMENTS

Figure 1:
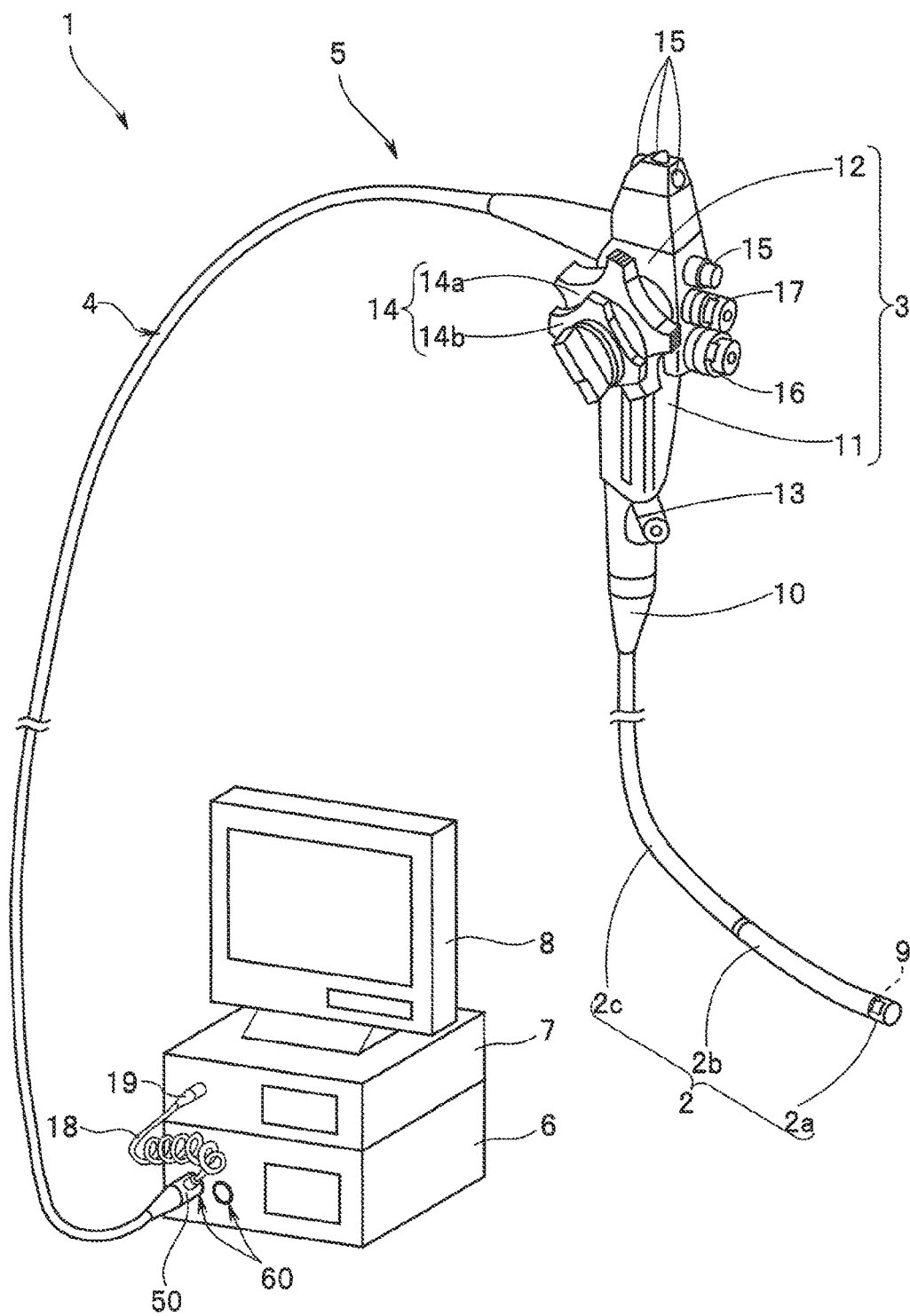
FIG. 1 is a schematic configuration diagram illustrating the overall configuration of an endoscope system to which the present invention is applied.

Hereunder, the present invention is described by way of embodiments that are illustrated in the accompanying drawings. The respective drawings used for the following description are drawings that schematically illustrate the present invention, and the dimensional relation between the respective members and the contraction scale and the like are varied for each component so as to show the respective components in a size that is recognizable in the drawings. Accordingly, the present invention is not limited only to the quantity of components, the shapes of components, the ratios between the sizes of components, and the relative positional relationship between the respective components illustrated in each of the accompanying drawings.

Note that, in the following description, the term "connector" refers to a component for connecting or the like that is used to connect wires, for example, in an electronic circuit or the like to form an electronic circuit. Such connectors include plug connectors and receptacle connectors. In this case, the term "plug connector" refers to a component on a so-called "male side" that is arranged at an end part of a long cable. On the other hand, the term "receptacle connector" refers to a component on a so-called "female side" that is installed in the surface of a distribution board or the like of an external apparatus or the like. Note that, in the following description, a connector to be applied to a medical device such as an endoscope system is, in particular, referred to as a "connector for a medical device".

First, before describing the respective embodiments of the present invention in detail, as one example of a medical device to which a connector for a medical device is applied, the schematic configuration of an endoscope system will be described using FIG. 1 to FIG. 3.

FIG. 1 is a schematic configuration diagram illustrating the overall configuration of an endoscope system to which the present invention is applied. FIG. 2 is an enlarged perspective view of a principal portion that illustrates, in an enlarged manner, an endoscope connector (plug connector) on an endoscope side among connectors in the endoscope system to which the present invention is applied. FIG. 3 is an enlarged cross-sectional view of a principal portion that is a cross-sectional view illustrating connectors in the endoscope system to which the present invention is applied, and that illustrates a state in which the endoscope connector (plug connector) on the endoscope side in FIG. 2 is fitted into and connected to a receptacle connector on an external apparatus side.

As illustrated in FIG. 1, an endoscope system 1 as a medical device mainly includes an endoscope 5, a light source apparatus 6 and a video processor 7 as external apparatuses, and a color monitor 8 that is a display apparatus.

The endoscope 5 is configured to include an insertion portion 2, an operation portion 3 and a universal cable 4 and the like. An endoscope connector 50 is provided at an end part portion on the distal end side of the universal cable 4. The endoscope connector 50 is configured in the form of a plug connector (male side). The endoscope connector 50 is detachably connected to the light source apparatus 6 that is an external apparatus. Therefore, the light source apparatus 6 that is an external apparatus in the endoscope system as a medical device is configured to have a plurality of (two in the example in FIG. 1) receptacle connectors 60 (female side) as connectors for a medical device.

In the endoscope 5, the insertion portion 2 is an elongated long member that is to be inserted to a site to be observed. The insertion portion 2 includes a distal end portion 2a, a bending portion 2b, and a flexible tube portion 2c that are connected in series. An illumination optical system that includes a light guide (not shown) and an image pickup apparatus that includes an image pickup device and the like are contained inside the distal end portion 2a. The bending portion 2b is configured so as to bend in, for example, four directions, namely the upward, downward, left and right directions. The flexible tube portion 2c is a tube-shaped member that is long and has flexibility.

In the endoscope 5, the operation portion 3 is constituted by combining a first exterior body 11 and a second exterior body 12. For example, a treatment instrument insertion port 13 is provided in the first exterior body 11. A proximal end portion of the insertion portion 2 is integrally connected with and fixed to the distal end side of the first exterior body 11 through a bend preventing member 10.

A bending operation portion 14, various switches 15, an air/water feeding button 16 and a suction button 17 and the like are provided on the second exterior body 12. Bending operation knobs 14a and 14b for performing an operation to bend the bending portion 2b, for example, are provided in the bending operation portion 14. When a surgeon rotates, for example, the bending operation knob 14a in a predetermined direction, an unshown bending wire is pulled or slackened and the bending portion 2b performs a bending operation in the upward direction.

The various switches 15 include, for example, a release switch, a freeze switch, and an observation mode switching switch for switching between normal observation and fluorescence observation.

As described above, the endoscope connector 50 is a plug connector that is provided at an end part portion on the distal end side of the universal cable 4 and is configured to be detachably attached to a receptacle connector 60 that is provided on the face of a board on a front surface side of the light source apparatus 6 that is an external apparatus. The endoscope connector 50 is a connecting component for transmitting a light flux from a light source or electrical signals or the like by being connected to the endoscope 5 and external apparatuses (light source apparatus 6 and video processor 7 and the like). For this purpose, an electric cable 18 is extended from the side face of the endoscope connector 50. The electric cable 18 is connected to the video processor 7 through a connector for a processor 19.

A bend preventing member 9 for covering an outer circumferential portion of the universal cable 4 and maintaining the connection strength of the universal cable 4 and for also preventing damage due to a twist or the like with respect to the universal cable 4 is arranged on the proximal end side of the endoscope connector 50, that is, at a connection portion with the universal cable 4.

Figure 2:
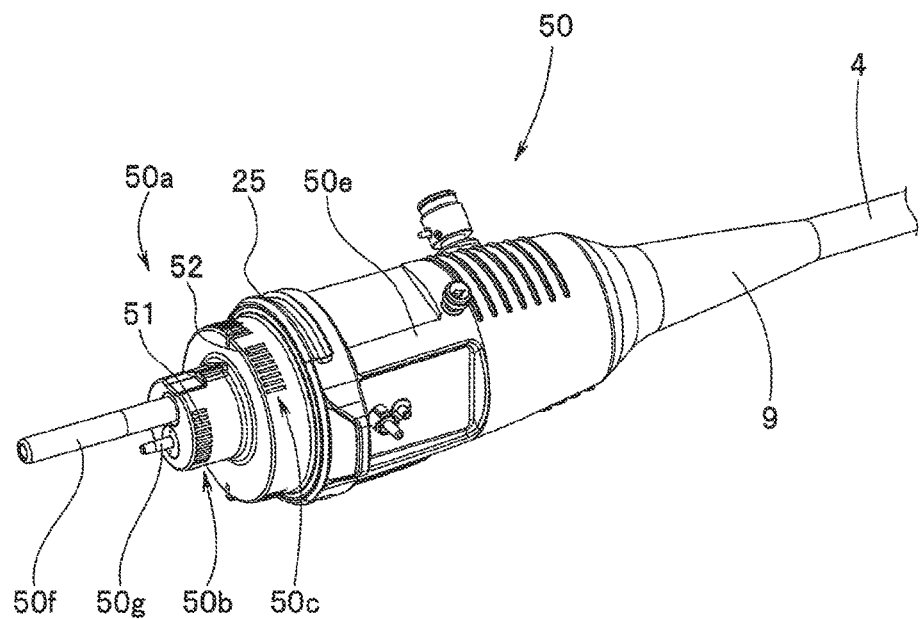
FIG. 2 is an enlarged perspective view of a principal portion that illustrates, in an enlarged manner, an endoscope connector (plug connector) on an endoscope side among connectors in the endoscope system illustrated in FIG. 1.
Figure 3:
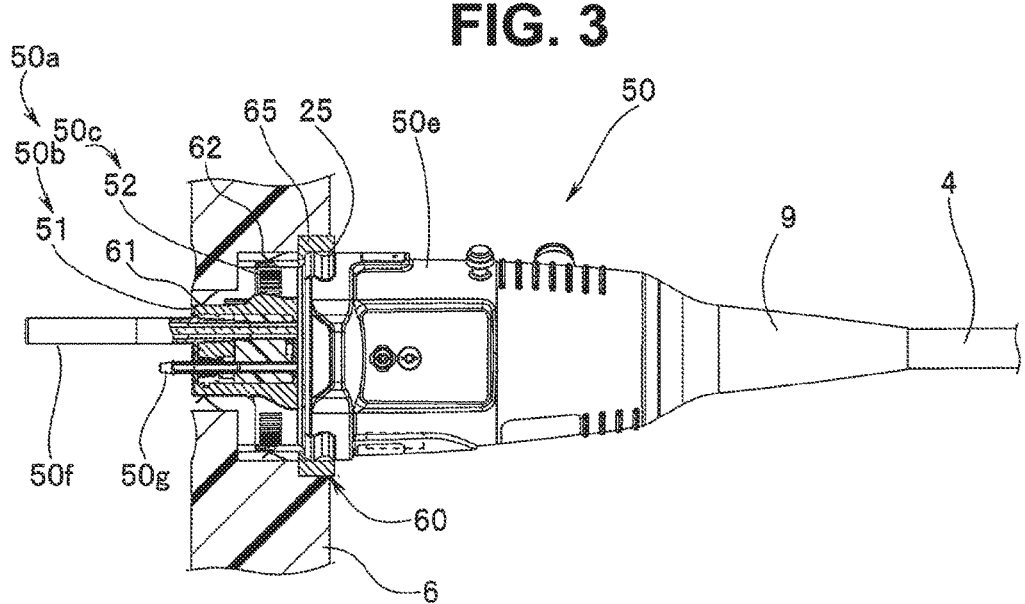
FIG. 3 is an enlarged cross-sectional view of a principal portion that illustrates connectors in the endoscope system illustrated in FIG. 1.

As illustrated in FIG. 2 and FIG. 3, the endoscope connector 50 mainly includes, in order from the distal end side: an electric plug portion 50a having two electrical connector portions 50b and 50c which are formed by being connectively provided in two stages, and are in substantially columnar shapes with mutually different outside diameters and integrally formed; a connector case 50e that is an exterior member of the endoscope connector 50 and is formed in a substantially cylindrical shape which is connectively provided at the electrical connector portion 50c on the proximal end side; and the bend preventing member 9.

Among the two electrical connector portions 50b and 50c that configure the electric plug portion 50a, the electrical connector portion (hereunder, referred to as "first electrical connector portion") 50b on the distal end side is formed to have a smaller diameter than a diameter of the electrical connector portion (hereunder, referred to as "second electrical connector portion") 50c on the proximal end side.

The first electrical connector portion 50b is formed to project from an end face of the second electrical connector portion 50c. Further, in a region at one part of the circumferential surface of the outer circumferential portion of the first electrical connector portion 50b, a plurality of first electric contact points 51 (which correspond to communication terminals that are described later) are provided side by side along the circumferential direction in a form in which a part of the first electric contact points 51 is exposed to outside. Further, a light guide pipe sleeve 50f on which an illuminating light from an external apparatus is incident and an air feeding pipe sleeve 50g through which a gas from an external apparatus is are provided in an extending condition from an end face of the first electrical connector portion 50b. In the second electrical connector portion 50c also, in a region at one part of the circumferential surface of the outer circumferential portion, a plurality of second electric contact points 52 (which correspond to communication terminals that are described later) are provided side by side along the circumferential direction in a form in which a part of the second electric contact points 52 is exposed to outside.

A plurality of pipe sleeve members is provided on an outer surface side of the connector case 50e. The pipe sleeve members are, for example, a water feeding pipe sleeve, a forward water feeding pipe sleeve, a pressurized pipe sleeve, a suction pipe sleeve, and a water leakage detection pipe sleeve (not specifically illustrated in the drawings) (see FIG. 2 and FIG. 3).

The bend preventing member 9 is provided on the proximal end side of the connector case 50e. The universal cable 4 is inserted through the bend preventing member 9 and introduced into the endoscope connector 50.

Inside the endoscope connector 50, in addition to a frame member made of metal that serves as a framework component, electrical constituent members such as an electronic circuit board are housed and disposed. Further, fluid piping (air/water feeding conduits) and an optical transmitting member (light guide cable) and the like are also inserted through the inside of the endoscope connector 50.

Note that, cutout portions are formed at two places at an upper part and a lower part in an outer circumferential edge of one end portion (site between the connector case 50e and the aforementioned electric plug portion 50a) of the connector case 50e, and a flange portion 25 (which corresponds to a grounding terminal that is described later) that is one part of the aforementioned metal frame member is exposed to outside from the cutout portions.

The flange portion 25 is configured so that grounds of the endoscope 5 and the light source apparatus 6 (external apparatus) that are described later are connected as a result of contacting a ground connection terminal 65 of the receptacle connector 60 when the endoscope connector 50 is fitted into and connected to the receptacle connector 60 of the light source apparatus 6 (external apparatus).

Further, the aforementioned plurality of electric contact points (51, 52) of the two electrical connector portions (50b, 50c), a plurality of contact pins which are electrically brought into conduction with the plurality of electric contact points (51, 52), and a plurality of electric boards on which the plurality of contact pins are fixed by soldering (none of which are illustrated in the drawings) are arranged inside the electric plug portion 50a. Note that, since the internal configuration of the electric plug portion 50a is a portion that is not directly related to the present invention, a detailed description and illustration of the internal configuration of the electric plug portion 50a is omitted herein. The endoscope system 1 is configured as described above.

Embodiments regarding the endoscope connector 50 configured in the form of a plug connector, and the receptacle connector 60 as a connector for a medical device in the light source apparatus 6 (external apparatus) in the endoscope system 1 configured in this manner are described in detail hereunder.

First Embodiment

Figure 4:
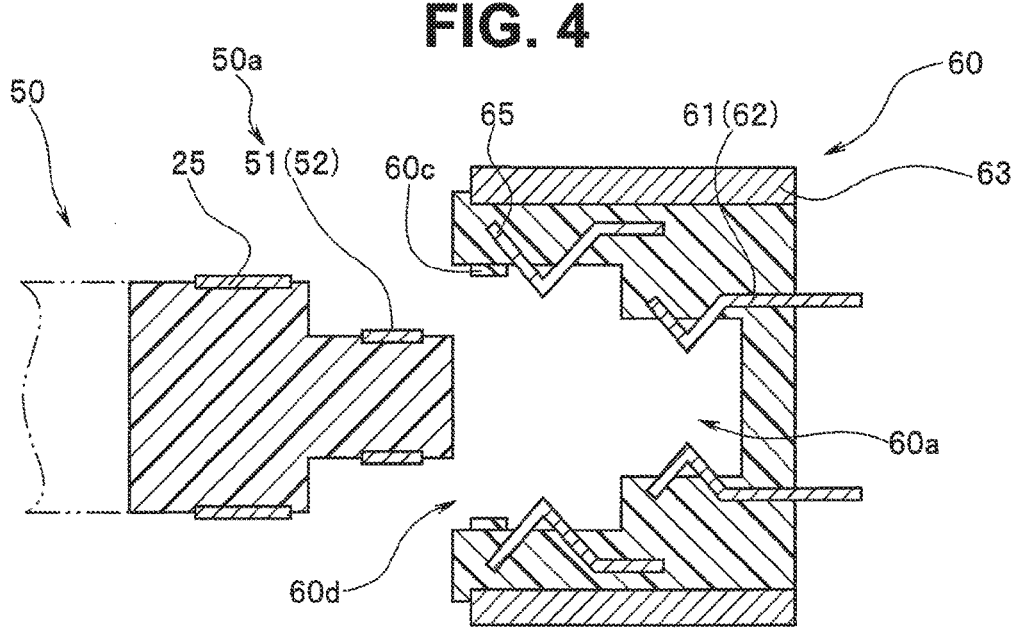
FIG. 4 is a cross-sectional view that conceptually illustrates a configuration in a non-interfitting state in which a plug connector and a receptacle connector in a connector for a medical device of a first embodiment of the present invention are not fitted together.
Figure 5:
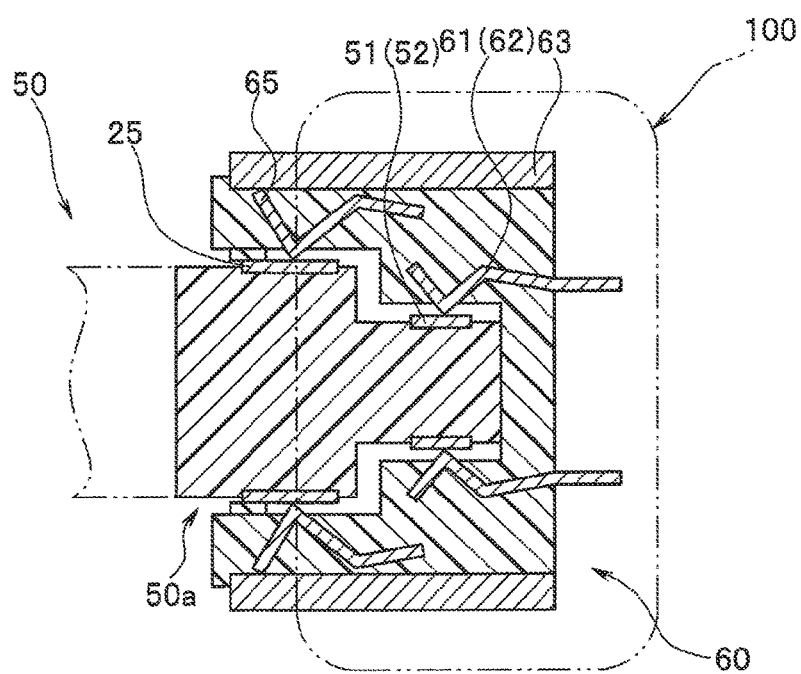
FIG. 5 is a cross-sectional view that conceptually illustrates a configuration in an interfitting state between the plug connector and the receptacle connector in the connector for a medical device illustrated in FIG. 4.

FIG. 4 and FIG. 5 are cross-sectional views that conceptually illustrate the configuration of a connector for a medical device of a first embodiment of the present invention. Among these drawings, FIG. 4 illustrates a non-interfitting state in which the plug connector is not fitted into the receptacle connector in the connector for a medical device of the present embodiment. Further, FIG. 5 illustrates a connected state in which the plug connector is fitted into the receptacle connector in the connector for a medical device of the present embodiment.

As described above, the connector for a medical device of the present embodiment is constituted by the endoscope connector 50 having the form of a male-side plug connector that is provided on the endoscope 5 side, and the female-side receptacle connector 60 that is provided on the light source apparatus 6 (external apparatus) side.

Among these connectors, the endoscope connector 50 includes the first electrical connector portion 50b having the plurality of first electric contact points 51, the second electrical connector portion 50c having the plurality of second electric contact points 52, and the flange portion 25 (grounding terminal) that is one part of the metal frame member that is a site to be connected to a ground.

The aforementioned plurality of first electric contact points 51 and the aforementioned plurality of second electric contact points 52 are each terminal portions for transmitting and communicating data, and are terminals for communication which are configured to conduct data communication between the endoscope 5 and the external apparatuses (light source apparatus 6, video processor 7), that is, are communication terminals.

Further, the flange portion 25 is a part of the metal frame member, and is a grounding terminal for reducing noise during data communication by being grounded.

Note that, in FIG. 4 and FIG. 5, the shape of the endoscope connector 50 is conceptually illustrated in a manner in which illustration of the configuration of a part of the endoscope connector 50, that is, constituent members (the aforementioned light guide pipe sleeve 50f and air feeding pipe sleeve 50g) that are extended from the end face of the first electrical connector portion 50b is omitted. Further, with respect to the plurality of electric contact points (51, 52) of the aforementioned two electrical connector portions (50b, 50c) and communication contact terminals (61, 62) corresponding thereto, in the drawings the electric contact points (51, 52) and the communication contact terminals (61, 62) are combined together and illustrated as a single member, respectively, to simplify the illustration (see reference numerals 51 and 61).

On the other hand, the receptacle connector 60 is a connector (connecting component) that is provided in the face of a board on the front face side of the light source apparatus 6 (external apparatus), and is configured so that the endoscope connector 50 (plug connector) can be fitted into the receptacle connector 60. Therefore, the receptacle connector 60 includes an opening portion 60d, a fitting portion 60a, a grounding portion 63, a communication contact terminal 61 and the ground connection terminal 65.

In the receptacle connector 60, the opening portion 60d is an opening that is formed in the face of the board on the front face side of the light source apparatus 6 (external apparatus) and that allows the outside and inside to communicate with each other. The opening portion 60d is formed to have a diameter of a size that is capable of accepting at least an outer diameter portion of the flange portion 25 of the endoscope connector 50 (plug connector).

Note that, at an inner edge portion of the opening portion 60d, an inward flange portion 60c is provided that is formed so as to project toward the inner side in the radial direction of the opening portion 60d. The inward flange portion 60c is formed so as not to hinder insertion of the endoscope connector 50 into the opening portion 60d when the endoscope connector 50 is fitted into the receptacle connector 60. In addition, the inward flange portion 60c is provided in order to restrict entry of a foreign body or the like into the opening portion 60d when the endoscope connector 50 is not fitted into the receptacle connector 60, and to also prevent a foreign body or the like that entered from the opening portion 60d from acting on the ground connection terminal 65 and deforming the ground connection terminal 65 and thereby causing the ground connection terminal 65 to come in contact with the grounding portion 63.

The fitting portion 60a is a site that corresponds to the endoscope connector 50 and is configured so that the endoscope connector 50 (plug connector) can be fitted into the fitting portion 60a. The fitting portion 60a is formed so as to correspond to the shape of the electrical connector portion 50a.

The grounding portion 63 is a constituent member configured to ground the flange portion 25 (grounding terminal) by being electrically connected to the flange portion 25. The grounding portion 63 is made from an electrically conductive member such as metal that is connected to an internal ground circuit (a ground portion as a reference potential point) inside the casing of the light source apparatus 6 that is an external apparatus. The grounding portion 63 is arranged in the receptacle connector 60 at a position in the vicinity of the outer circumferential side of the fitting portion 60a so as to extend in a direction that is along the insertion direction at a time when the endoscope connector 50 is fitted into the receptacle connector 60.

The communication contact terminal 61 is a terminal member configured to be electrically connected to the electric contact points 51 (communication terminal) when the endoscope connector 50 has been fitted into the fitting portion 60a. The communication contact terminal 61 is connected to an internal electronic circuit of the light source apparatus 6 which is an external apparatus or to an internal electronic circuit of the video processor 7 which is an external apparatus that is connected through the electric cable 18 and the connector for a processor 19. The communication contact terminal 61 is formed so as to be capable of deforming under stress produced by the endoscope connector 50 (plug connector) when the receptacle connector 60 and the endoscope connector 50 (plug connector) are fitted together. Therefore, the communication contact terminal 61, for example, is formed of a metallic material having a thin plate shape or linear shape that has elasticity, and is formed in an elastically deformable manner. The entire communication contact terminal 61 is arranged inside the receptacle connector 60, and is disposed in a form such that a part of the communication contact terminal 61 projects toward the inside relative to an inner wall surface of the fitting portion 60a. Further, the communication contact terminal 61 is configured so as to deform and move in a direction that is approximately perpendicular to the insertion direction at a time when the endoscope connector 50 is fitted into the receptacle connector 60.

The ground connection terminal 65 is a terminal member that interposes between the grounding portion 63 and the flange portion 25 (grounding terminal) in operative association with interfitting of the fitting portion 60a and the endoscope connector 50 to electrically connect the grounding portion 63 and the flange portion 25 (grounding terminal).

In a non-interlining state (normal state) in which the endoscope connector 50 (plug connector) is not fitted into the receptacle connector 60, the ground connection terminal 65 is in a non-contact state with respect to the grounding portion 63. On the other hand, in an interfitting state in which the electric plug portion 50a of the endoscope connector 50 (plug connector) has been fitted into the fitting portion 60a of the receptacle connector 60, the ground connection terminal 65 is configured to deform under stress that is applied by the endoscope connector 50 (plug connector) so as to be electrically connected with the grounding portion 63.

Therefore, the ground connection terminal 65, for example, constitutes a so-called "finger terminal" which is formed of a metallic material having a thin plate shape or linear shape that has elasticity, and is formed in an elastically deformable manner. The entire ground connection terminal 65 is disposed inside the receptacle connector 60, and is disposed in a form such that a part of the ground connection terminal 65 projects toward the inside relative to an inner wall surface of a second fitting portion 60b. Further, the ground connection terminal 65 is also configured so as to deform and move in a direction that is approximately perpendicular to the insertion direction at a time when the endoscope connector 50 is fitted into the receptacle connector 60.

In the receptacle connector 60 configured as described above, when the state is one in which the endoscope connector 50 is not fitted and connected to the receptacle connector 60, as illustrated in FIG. 4, the ground connection terminal 65 and the grounding portion 63 are in a non-contact state. That is, when fitting and connection between the endoscope connector 50 in the form of a plug connector and the receptacle connector 60 are being released, such an action serves to electrically separate the grounding portion 63 and the flange portion 25 (grounding terminal).

The action at a time when the endoscope connector 50 is fitted into and connected to the receptacle connector 60 will now be described in detail.

First, in the state illustrated in FIG. 4, that is, when the receptacle connector 60 and the endoscope connector 50 are in a non-interfitting state, the electric plug portion 50a on the distal end side of the endoscope connector 50 (plug connector) is inserted into the opening portion 60d of the receptacle connector 60. The electric plug portion 50a of the endoscope connector 50 is then fitted into the fitting portion 60a of the receptacle connector 60.

In this case, in the state before the two components are fitted together, the receptacle connector 60 is in the normal state, and at this time the ground connection terminal 65 and the grounding portion 63 are in a non-contact state as described above. During the course of the electric plug portion 50a advancing from this state to enter the fitting portion 60a from the opening portion 60d, the electric contact points 51 contact the communication contact terminal 61, and when the endoscope connector 50 is pushed in further, the electric plug portion 50a advances further to the inner part while causing the communication contact terminal 61 to deform and while also maintaining the contact state between the electric contact points 51 and the communication contact terminal 61.

Simultaneously, during the course of the aforementioned fitting process, the flange portion 25 contacts the ground connection terminal 65. When the endoscope connector 50 is pushed in further, the electric plug portion 50a advances further to the inner part while causing the ground connection terminal 65 to deform and while also maintaining the contact state between the flange portion 25 and the ground connection terminal 65. Thus, as the action of fitting the endoscope connector 50 into the receptacle connector 60 progresses, in operative association with the fitting action, the ground connection terminal 65 deforms and a part of the ground connection terminal 65 approaches the grounding portion 63. When in due course the electric plug portion 50a is completely fitted into and connected to the fitting portion 60a, the ground connection terminal 65 contacts the grounding portion 63. By this means, the flange portion 25 (grounding terminal) is electrically connected with the grounding portion 63 through the ground connection terminal 65.

In this case, the state in which the endoscope connector 50 and the receptacle connector 60 are in the course of being fitted together is a state in which an interfitting state is not formed therebetween, and hence the ground connection terminal 65 and the grounding portion 63 are in a non-contact state. Therefore, the grounding portion 63 and the flange portion 25 (grounding terminal) are electrically separated. Subsequently, when the ground connection terminal 65 and the grounding portion 63 come into contact upon the electric plug portion 50a being completely fitted into and connected to the fitting portion 60a, the grounding portion 63 and the flange portion 25 (grounding terminal) are electrically connected through the ground connection terminal 65. The state at this time is the state illustrated in FIG. 5.

In this way, as illustrated in FIG. 5, when the endoscope connector 50 (plug connector) and the receptacle connector 60 are fitted and connected together, the flange portion 25 (grounding terminal) is connected through the ground connection terminal 65 to the grounding portion 63. At this time, an electromagnetic shield in a region denoted by reference numeral 100 in FIG. 5 is formed in a surrounding region that includes the connecting portion between the electric contact points 51 (communication terminals) and the communication contact terminal 61.

The electromagnetic shield 100 is formed as a shield for shielding noise that is a shield which is generated upon the ground connection terminal 65 and the grounding portion 63 that are provided on the receptacle connector 60 side and the flange portion 25 on the endoscope connector 50 side being connected.

According to the first embodiment configured as described above, when the endoscope connector 50 (plug connector) and the receptacle connector 60 are fitted together, the grounding portion 63 is connected through the ground connection terminal 65 of the receptacle connector 60 with the flange portion 25 of the endoscope connector 50 and an electromagnetic shield is thereby formed. On the other hand, when the endoscope connector 50 (plug connector) and the receptacle connector 60 are not fitted together, the ground connection terminal 65 and the grounding portion 63 of the receptacle connector 60 are in a non-contact state and are not connected, and hence the ground connection terminal 65 can be placed in a non-grounded state.

Since the ground connection terminal 65 is configured so as to deform under stress applied by the electric plug portion 50a of the endoscope connector 50 when the endoscope connector 50 (plug connector) is fitted into the receptacle connector 60, the ground connection terminal 65 can be electrically connected to the grounding portion 63 merely by inserting and fitting the endoscope connector 50 (plug connector) in the receptacle connector 60.

Therefore, according to this configuration, in the connector for a medical device of the present embodiment, when a plug connector (endoscope connector 50) is connected to the receptacle connector 60 in an external apparatus (light source apparatus 6, video processor 7, or the like) that includes a plurality of the receptacle connectors 60 in a medical device such as the endoscope system 1, the ground connection terminal 65 and the flange portion 25 (grounding terminal) are electrically connected to form an electromagnetic shield. On the other hand, when the receptacle connector 60 and the endoscope connector 50 (plug connector) are not connected, an internal ground circuit (ground portion as a reference potential point) and the ground connection terminal 65 provided inside the fitting portion on the receptacle connector 60 side can be placed in an electrically separated state.

Further, according to the present embodiment, the present invention can be applied without particular configurational changes with respect to the endoscope connector 50. Therefore, an endoscope connector of a conventional form can be applied in its existing form.

Second Embodiment

Figure 6:
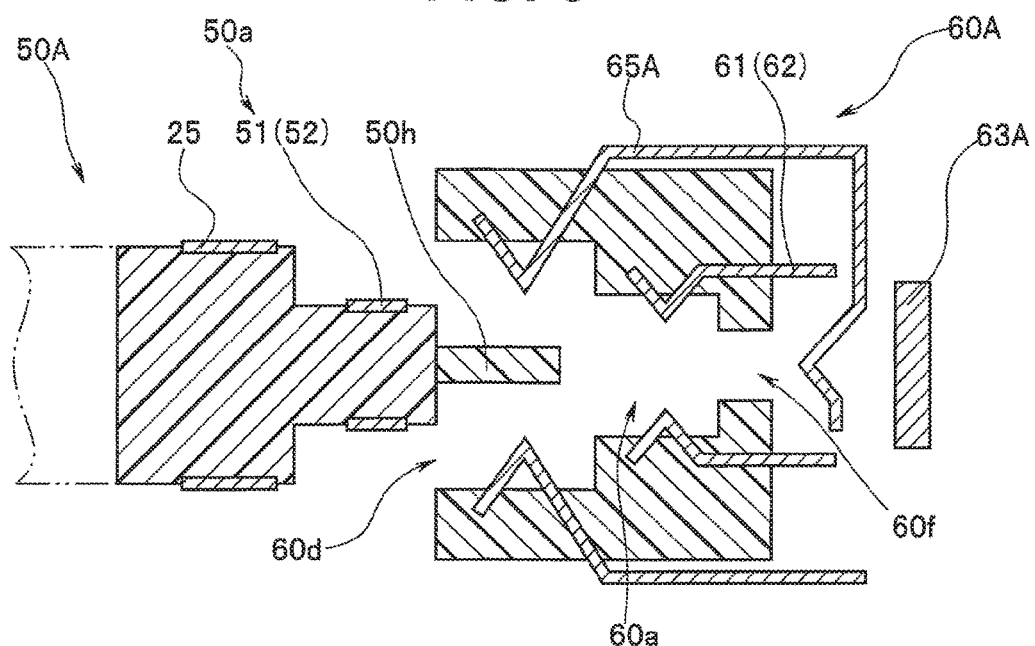
FIG. 6 is a cross-sectional view that conceptually illustrates a configuration in a non-interfitting state in which a plug connector and a receptacle connector in a connector for a medical device of a second embodiment of the present invention are not fitted together.
Figure 7:
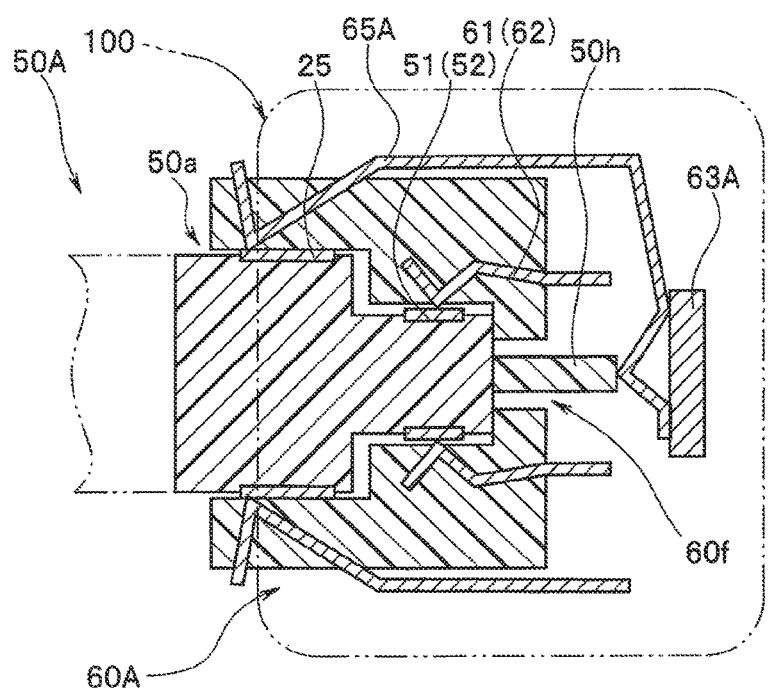
FIG. 7 is a cross-sectional view that conceptually illustrates a configuration in an interfitting state between the plug connector and the receptacle connector in the connector for a medical device illustrated in FIG. 6.

Next, a connector for a medical device of a second embodiment of the present invention will be described below. FIG. 6 and FIG. 7 are cross-sectional views that conceptually illustrate the configuration of a connector for a medical device according to a second embodiment of the present invention. Among these figures, FIG. 6 illustrates a non-interfitting state in which a plug connector is not fitted into a receptacle connector in the connector for a medical device of the present embodiment. Further, FIG. 7 illustrates a connected state in which the plug connector is fitted into the receptacle connector in the connector for a medical device of the present embodiment.

The fundamental configuration of the connector for a medical device of the present embodiment is substantially the same as the configuration in the above described first embodiment. In the present embodiment, with respect to an endoscope connector 50A having the form of a plug connector as the male side that is provided on the endoscope 5 side, the only difference from the endoscope connector 50 of the above described first embodiment is that a pressing protrusion portion 50h is provided in a protruding condition at the distal end portion of the electric plug portion 50a. As illustrated in FIG. 6 and FIG. 7, the pressing protrusion portion 50h is a rod-shaped portion that is formed so as to protrude in the insertion direction at a time when the endoscope connector 50A is fitted into a receptacle connector 60A. The pressing protrusion portion 50h is formed to have a shape, size and arrangement such that the pressing protrusion portion 50h can be inserted through a through-hole 60f (described later) that is formed in a bottom face portion of the fitting portion 60a. The remaining configuration of the endoscope connector 50A is the same as in the above described first embodiment.

On the other hand, in the present embodiment, the configuration of the receptacle connector 60A as the female side that is provided on the light source apparatus 6 (external apparatus) side differs somewhat from the configuration of the receptacle connector 60 in the above described first embodiment. Therefore, components that are substantially the same as components in the above described first embodiment are denoted by the same reference numerals as in the first embodiment and a description of such components is omitted hereunder, and only portions that are different from the first embodiment are described in detail.

In the connector for a medical device of the present embodiment, similarly to the above described first embodiment, the receptacle connector 60A is a connector (connecting component) that is provided on the face of a board on the front face side of the light source apparatus 6 (external apparatus; see FIG. 1) and is configured so that the endoscope connector 50A can be fitted into the receptacle connector 60A. Therefore, the receptacle connector 60A includes the opening portion 60d, the fitting portion 60a, a grounding portion 63A, the communication contact terminal 61 and a ground connection terminal 65A.

In the receptacle connector 60A, the opening portion 60d is an opening that is the same as the opening portion in the above described first embodiment. Note that, the inward flange portion 60c of the above described first embodiment is not provided in the opening portion 60d of the present embodiment. This is because the inward flange portion 60c is unnecessary in the configuration of the present embodiment since, when the endoscope connector 50A has not been fitted into the receptacle connector 60A, even if a foreign body or the like that entered from the opening portion 60d acts on the ground connection terminal 65A, there is no risk of the ground connection terminal 65A contacting the grounding portion 63A.

The fitting portion 60a is formed similarly to the fitting portion in the aforementioned first embodiment. In the present embodiment, the through-hole 60f is additionally formed in the bottom face portion of the fitting portion 60a on the distal end side. The through-hole 60f is formed as a through-hole which the pressing protrusion portion 50h on the endoscope connector 50A side is inserted through when the endoscope connector 50A is fitted into the receptacle connector 60A.

The grounding portion 63A is the same as the grounding portion 63 in the foregoing first embodiment with respect to the functional aspect that the grounding portion 63A is a constituent member configured to ground the flange portion 25 (grounding terminal) as a connection object by being electrically connected. Similarly to the first embodiment, the grounding portion 63A is made from an electrically conductive member such as metal that is connected to an internal ground circuit (a ground portion as a reference potential point) inside the casing of the light source apparatus 6 (external apparatus), and is arranged in the vicinity of the fitting portion 60a in the receptacle connector 60A. Note that, the grounding portion 63A of the present embodiment is fixedly installed at a position facing the through-hole 60f in the receptacle connector 60A, that is a position in the vicinity of the fitting portion 60a and which is a recessed position along the insertion direction at a time when the endoscope connector 50A is fitted into the receptacle connector 60A.

The communication contact terminal 61 is configured completely the same as in the above described first embodiment.

The ground connection terminal 65A electrically connects the grounding portion 63A and the flange portion 25 (grounding terminal) in operative association with interfitting of the fitting portion 60a and the endoscope connector 50A, and is therefore the same as in the foregoing first embodiment with respect to the functional aspect that the ground connection terminal 65A is a terminal member that interposes between the grounding portion 63A and the flange portion 25 (grounding terminal).

In the present embodiment, one end of the ground connection terminal 65A is provided in a protruding condition on the inner circumferential surface of the fitting portion 60a and has a contact portion that comes in contact with the flange portion 25 (grounding terminal), and the ground connection terminal 65A is disposed so as to extend from the contact portion and extend around the interior of the receptacle connector 60A, with the other end of the ground connection terminal 65A being disposed in the vicinity of the grounding portion 63A in a space between the grounding portion 63A and the through-hole 60f. In this case, the other end of the ground connection terminal 65A is formed in a cantilever shape and is configured to be elastically deformable in the insertion direction at a time when the endoscope connector 50A is fitted into the receptacle connector 60A.

By means of this configuration, in a non-interfitting state in which the endoscope connector 50A has not been fitted into the receptacle connector 60A, the other end of the ground connection terminal 65A is in a non-contact state with respect to the grounding portion 63A. On the other hand, in an interfitting state in which the electric plug portion 50a of the endoscope connector 50A has been fitted into the fitting portion 60a of the receptacle connector 60A, the ground connection terminal 65A is configured so as to deform by being pressed by the pressing protrusion portion 50h at the distal end of the endoscope connector 50A and to be thereby electrically connected with the grounding portion 63A.

Therefore, the ground connection terminal 65A, for example, is formed of a metallic material having a thin plate shape or linear shape that has elasticity. Further, a part on the one end side of the ground connection terminal 65A is disposed in a form in which the part projects toward the inside relative to the inner wall surface of a second fitting portion 60b, and is configured so as to deform and move in a direction that is approximately perpendicular to the insertion direction at a time when the endoscope connector 50A is fitted into the receptacle connector 60A. Further, as described above, a part on the other end side of the ground connection terminal 65A is disposed in a space between the grounding portion 63A and the through-hole 60f so as to be elastically deformable in the insertion direction at a time when the endoscope connector 50A is fitted into the receptacle connector 60A.

In the receptacle connector 60A of the present embodiment that is configured in the above described manner also, as illustrated in FIG. 6, the ground connection terminal 65A and the grounding portion 63A are in a non-contact state in a state in which the endoscope connector 50A has not been fitted into and connected to the receptacle connector 60A. That is, when the fitting and connection between the endoscope connector 50A and the receptacle connector 60A are being released, the grounding portion 63A and the flange portion 25 are electrically separated.

The action at a time when the endoscope connector 50A is fitted into and connected to the receptacle connector 60A will now be described in detail.

First, in the state illustrated in FIG. 6, that is, when the receptacle connector 60A and the endoscope connector 50A are in a non-interfitting state, the electric plug portion 50a on the distal end side of the endoscope connector 50A is inserted into the opening portion 60d of the receptacle connector 60A. The electric plug portion 50a of the endoscope connector 50A is then fitted into fitting portion 60a of the receptacle connector 60A.

In this case, in the state before the two components are fitted together, the receptacle connector 60A is in the normal state, and at this time the other end of the ground connection terminal 65A and the grounding portion 63 are in a non-contact state (FIG. 6). During the course of the electric plug portion 50a advancing from this state to enter the fitting portion 60a from the opening portion 60d, the electric contact points 51 contact the communication contact terminal 61, and when the endoscope connector 50A is pushed in further, the electric plug portion 50a advances further to the inner part while causing the communication contact terminal 61 to deform and while also maintaining the contact state between the electric contact points 51 and the communication contact terminal 61. Note that, the connecting action between the communication contact terminal 61 and the electric contact points 51 up to this point is the same as in the above described first embodiment.

Simultaneously, during the course of the aforementioned fitting process, the flange portion 25 contacts the around connection terminal 65A. Subsequently, upon the endoscope connector 50A being pushed in further, the electric plug portion 50a advances further to the inner part while causing the around connection terminal 65A to deform and while also maintaining the contact state between the flange portion 25 and the one end of the ground connection terminal 65A.

Upon the endoscope connector 50A being pushed in further in this way, the pressing protrusion portion 50h at the distal end of the electric plug portion 50a of the endoscope connector 50A is inserted through the through-hole 60f. Thereupon, the distal end of the pressing protrusion portion 50h contacts the other end of the ground connection terminal 65A, and presses and deforms the other end of the ground connection terminal 65A. The other end of the ground connection terminal 65A thereby approaches the grounding portion 63A. When in due course the electric plug portion 50a is completely fitted into and connected to the fitting portion 60a, the other end of the ground connection terminal 65A contacts the grounding portion 63A. By this means, the flange portion 25 (grounding terminal) is electrically connected with the grounding portion 63A through the ground connection terminal 65A.

In this case, while the endoscope connector 50A and the receptacle connector 60A are in the course of being fitted together, the grounding portion 63A and the flange portion 25 are electrically separated. On the other hand, when the electric plug portion 50a is completely fitted into and connected to the fitting portion 60a, the grounding portion 63A and the flange portion 25 are electrically connected through the ground connection terminal 65A as a result of the other end of the ground connection terminal 65A and the grounding portion 63A coming in contact with each other. The state at this time is the state illustrated in FIG. 7.

In this way, as illustrated in FIG. 7, when the endoscope connector 50A and the receptacle connector 60A are fitted and connected together, the flange portion 25 is connected through the ground connection terminal 65A to the grounding portion 63A. At this time, similarly to the above described first embodiment, an electromagnetic shield in a region denoted by reference numeral 100 in FIG. 7 is formed in a surrounding region including the connecting portion between the electric contact points 51 (communication terminals) and the communication contact terminal 61.

According to the second embodiment configured as described above, the same advantageous effects as the advantageous effects of the above described first embodiment can be obtained.

Further, according to the present embodiment, a configuration is adopted so that, by an insertion action for fitting the endoscope connector 50A into the receptacle connector 60, the pressing protrusion portion 50h at the distal end of the electric plug portion 50a of the endoscope connector 50A is inserted through the through-hole 60f, and the distal end of the pressing protrusion portion 50h presses the other end of the ground connection terminal 65A that is at a recessed position to thereby deform the other end of the ground connection terminal 65A to cause the ground connection terminal 65A to contact the grounding portion 63A.

By means of this configuration, when the endoscope connector 50A and the receptacle connector 60A are in a non-interfitting state, even if a foreign body or the like that entered from the opening portion 60d of the receptacle connector 60A acts on the ground connection terminal 65A, there is no risk of the ground connection terminal 65A contacting the grounding portion 63A.

Accordingly, when the endoscope connector 50A and the receptacle connector 60A are in a non-interfitting state, an electrically separated state between the grounding portion 63A and the flange portion 25 can be reliably ensured.

Note that, unlike the above described first embodiment, the present embodiment also involves a certain number of configurational changes with respect to the endoscope connector 50A.

Third Embodiment

Figure 8:
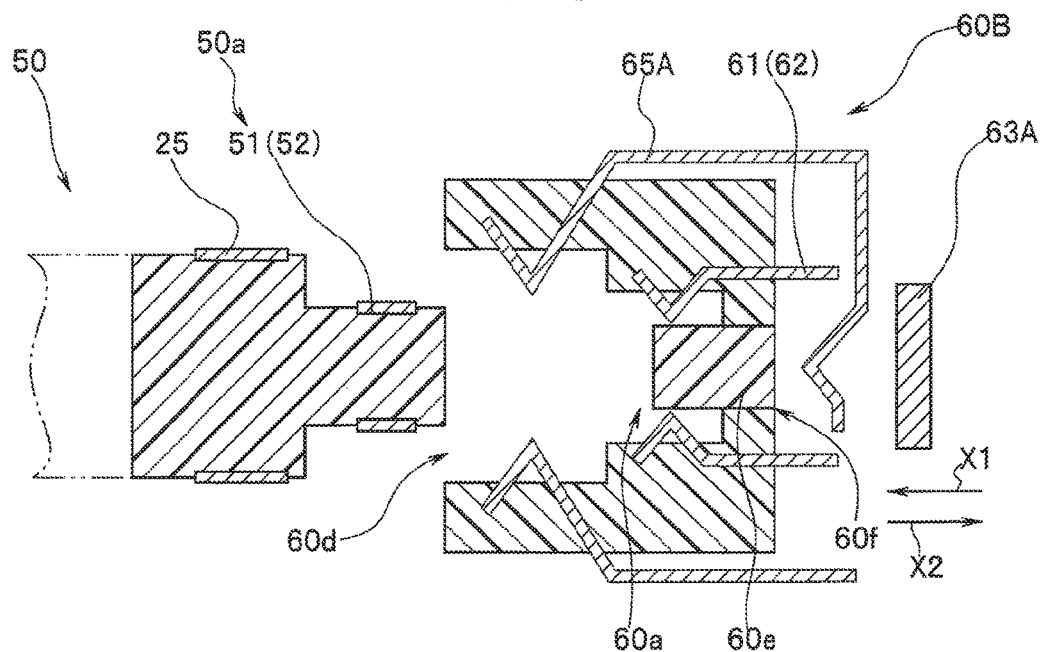
FIG. 8 is a cross-sectional view that conceptually illustrates a configuration in a non-interfitting state in which a plug connector and a receptacle connector in a connector for a medical device of a third embodiment of the present invention are not fitted together.
Figure 9:
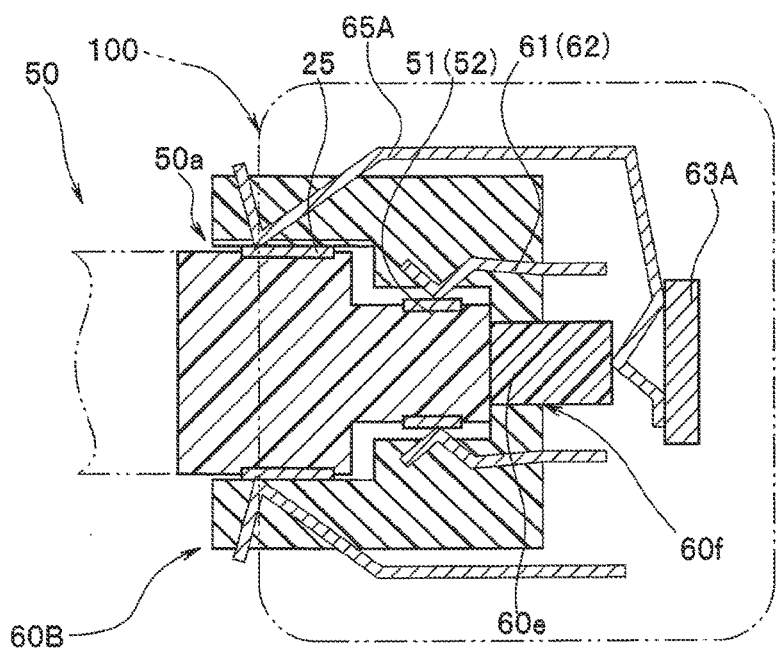
FIG. 9 is a cross-sectional view that conceptually illustrates a configuration in an interfitting state between the plug connector and the receptacle connector in the connector for a medical device illustrated in FIG. 8.

Next, a connector for a medical device according to a third embodiment of the present invention will be described. FIG. 8 and FIG. 9 are cross-sectional views that conceptually illustrate the configuration of a connector for a medical device according to a third embodiment of the present invention. Among these figures, FIG. 8 illustrates a non-interfitting state in which a plug connector is not fitted into a receptacle connector in the connector for a medical device of the present embodiment. Further, FIG. 9 illustrates a connected state in which the plug connector is fitted into the receptacle connector in the connector for a medical device of the present embodiment.

The fundamental configuration of the connector for a medical device of the present embodiment is substantially the same as the configurations in the respective embodiments described above. In the present embodiment, the configuration of the endoscope connector 50 having the form of a plug connector as the male side that is provided on the endoscope 5 side is completely the same as in the above described first embodiment. Accordingly, a description of the configuration of the endoscope connector 50 is omitted hereunder.

On the other hand, in the present embodiment, the configuration of a receptacle connector 60B as the female side that is provided on the light source apparatus 6 (external apparatus) side differs somewhat from the configurations of the receptacle connectors in the respective embodiments described above. Therefore, components that are substantially the same as components in the respective embodiments described above are denoted by the same reference numerals as in the respective embodiments described above and a description of such components is omitted hereunder, and only portions that are different from the foregoing embodiments are described in detail.

In the connector for a medical device of the present embodiment, similarly to the above described second embodiment, the receptacle connector 60B is a connector (connecting component) that is provided on the face of a board on the front face side of the light source apparatus 6 (external apparatus; see FIG. 1) and is configured so that the endoscope connector 50 can be fitted into the receptacle connector 60B. Therefore, the receptacle connector 60B includes the opening portion 60*d*, the fitting portion 60*a*, the grounding portion 63A, the communication contact terminal 61 and the ground connection terminal 65A.

In the receptacle connector 60B, the opening portion 60*d* has completely the same configuration as in the above described second embodiment. Hence, the inward flange portion 60*c* provided in the above described first embodiment is not provided in the opening portion 60*d* of the present embodiment. This is because the inward flange portion 60*c* is not required for the same reason as in the configuration of the second embodiment that is described above.

The fitting portion 60*a* is formed similarly to the fitting portion 60*a* in the above described second embodiment. In the present embodiment also, similarly to the above described second embodiment, the through-hole 60*f* is formed in the bottom face portion of the fitting portion 60*a*. In the present embodiment, furthermore, in the through-hole 60*f*, a moving member 60*e* is disposed that is capable of protruding and retracting along the penetrating direction of the through-hole 60*f*, that is, along the insertion direction when the endoscope connector 50 is fitted into the receptacle connector 60B. The moving member 60*e* is an intermediate member that is interposed so that, when the endoscope connector 50 is fitted into the receptacle connector 60B, the moving member 60*e* is pressed by the distal end of the endoscope connector 50 and thereby presses and deforms the other end of the ground connection terminal 65A to connect the ground connection terminal 65A to the grounding portion 63A. Note that, although not illustrated in the drawings, in the normal state (non-interfitting state) illustrated in FIG. 8, the moving member 60*e* is urged in the direction of an arrow X1 in FIG. 8 by unshown urging means so as to be disposed at a position at which the moving member 60*e* protrudes into the interior of the fitting portion 60*a*. According to this configuration, the moving member 60*e* also fulfills a role of preventing the occurrence of a situation in which, when the endoscope connector 50 and the receptacle connector 60B are in a non-interfitting state, a finger or the like of a person such as a user or a conductive material of various kinds of instruments unintentionally contacts the communication contact terminal 61.

The grounding portion 63A, the communication contact terminal 61 and the ground connection terminal 65A have the same configurations as in the above described second embodiment.

According to this configuration, in a non-interfitting state in which the endoscope connector 50 has not been fitted into the receptacle connector 60B, as illustrated in FIG. 8, the other end of the ground connection terminal 65A is in a non-contact state with respect to the grounding portion 63A. That is, when fitting and connection between the endoscope connector 50 and the receptacle connector 60B are released, the grounding portion 63A and the flange portion 25 are electrically separated. On the other hand, in an interfitting state in which the electric plug portion 50*a* of the endoscope connector 50 has been fitted into the fitting portion 60*a* of the receptacle connector 60B, the distal end of the endoscope connector 50 presses the moving member 60*e* to cause the moving member 60*e* to move in the direction of an arrow X2 in FIG. 8 and press the other end of the ground connection terminal 65A and cause the other end of the ground connection terminal 65A to deform and thereby electrically connect the other end of the ground connection terminal 65A and the grounding portion 63A.

The action at a time when the endoscope connector 50 is fitted into and connected to the receptacle connector 60B will now be described in detail.

First, in the state illustrated in FIG. 8, that is, when the receptacle connector 60B and the endoscope connector 50 are in a non-interfitting state, the electric plug portion 50*a* on the distal end side of the endoscope connector 50 is inserted into the opening portion 60*d* of the receptacle connector 60B. The electric plug portion 50*a* of the endoscope connector 50 is then fitted into the fitting portion 60*a* of the receptacle connector 60B.

In this case, in the state before the two components are fitted together, the receptacle connector 60B is in the normal state, and at this time the other end of the ground connection terminal 65A and the grounding portion 63A are in a non-contact state (FIG. 8). During the course of the electric plug portion 50*a* advancing from this state to enter the fitting portion 60*a* from the opening portion 60*d*, the electric contact points 51 contact the communication contact terminal 61. The connecting action between the communication contact terminal 61 and the electric contact points 51 at this time is the same as in the first and second embodiments that are described above.

Simultaneously, during the course of the aforementioned fitting process, the flange portion 25 contacts the ground connection terminal 65A. Subsequently, upon the endoscope connector 50 being pushed in further, the electric plug portion 50a advances further to the inner part while causing the ground connection terminal 65A to deform and while also maintaining the contact state between the flange portion 25 and the one end of the ground connection terminal 65A.

When the endoscope connector 50 is pushed in further in this way, the distal end of the endoscope connector 50 butts against the moving member 60e arranged in the through-hole 60f, and presses the moving member 60e. Thereupon, the moving member 60e moves within the through-hole 60f in the direction of the arrow X2 in FIG. 8, and the distal end of the moving member 60e contacts the other end of the ground connection terminal 65A and presses and deforms the other end of the ground connection terminal 65A. The other end of the ground connection terminal 65A then approaches the grounding portion 63A. When in due course the electric plug portion 50a is completely fitted into and connected to the fitting portion 60a, the other end of the ground connection terminal 65A contacts the grounding portion 63A. By this means, the flange portion 25 (grounding terminal) is electrically connected with the grounding portion 63A through the ground connection terminal 65A.

In this case, while the endoscope connector 50 and the receptacle connector 603 are in the course of being fitted together, the grounding portion 63A and the flange portion 25 are electrically separated. On the other hand, when the electric plug portion 50a is completely fitted into and connected to the fitting portion 60a, the grounding portion 63A and the flange portion 25 are electrically connected through the ground connection terminal 65A as a result of the other end of the ground connection terminal 65A and the grounding portion 63A coming in contact with each other. The state at this time is the state illustrated in FIG. 9.

In this way, as illustrated in FIG. 9, when the endoscope connector 50 and the receptacle connector 60B are fitted and connected together, the flange portion 25 is connected through the ground connection terminal 65A to the grounding portion 63A. At this time, similarly to the respective embodiments described above, an electromagnetic shield in a region denoted by reference numeral 100 in FIG. 9 is formed in a surrounding region including the connecting portion between the electric contact points 51 (communication terminals) and the communication contact terminal 61.

According to the third embodiment configured as described above, the same advantageous effects as the advantageous effects in the respective embodiments described above can be obtained. Further, according to the present embodiment, similarly to the above described first embodiment, since the configuration does not involve configurational changes with respect to the endoscope connector 50, an endoscope connector of a conventional form can be applied in its existing form.

Note that the present invention is not limited to the above described embodiments, and naturally various modifications and applications can be implemented within a range that does not deviate from the gist of the present invention. Further, the above described embodiments include inventions of various stages, and various inventions can be extracted by appropriately combining a plurality of the disclosed configuration requirements. For example, if a problem to be solved by the invention can be solved and the effects of the invention are obtained even after omitting some of the configuration requirements from all the configuration requirements described in an embodiment that is described above, then the configuration obtained by omitting the configuration requirements can be extracted as an invention. In addition, components from different embodiments may be appropriately combined. The present invention is not limited by a specific embodiment of the invention except that the invention is limited by the accompanying claims.

The present invention can be applied not only to endoscope apparatuses in the medical field but also to endoscope apparatuses in the industrial field.

What is claimed is:

1. A receptacle connector including a fitting portion into which a plug connector including a grounding terminal for forming an electromagnetic shield by being grounded can be fitted, the receptacle connector comprising:
    a grounding portion configured to ground a connection object by being electrically connected; and
    a ground connection terminal that is provided in the fitting portion and that is configured to be switchably held in a first state in which the ground connection terminal is electrically separated from the grounding portion when the fitting portion and the plug connector are not fitted together, or in a second state in which the ground connection terminal contacts and is electrically brought into conduction with the grounding portion when the fitting portion and the plug connector are fitted together;
wherein:
    the ground connection terminal being switched between the first state and the second state in operative association with interfitting of the plug connector and the fitting portion, and the ground connection terminal being configured such that the grounding terminal and the grounding portion are electrically separated at a time of the first state, and the grounding terminal and the grounding portion are electrically brought into conduction with each other through the ground connection terminal at a time of the second state; and
    switching from the first state to the second state in the ground connection terminal occurs as a result of deformation of the ground connection terminal that is caused by a pressing force generated by a distal end of the plug connector in a state in which the fitting portion is fitted into the plug connector.

* * * * *